US008137340B2

(12) United States Patent
Lai et al.

(10) Patent No.: US 8,137,340 B2
(45) Date of Patent: Mar. 20, 2012

(54) APPARATUS AND METHOD FOR SOFT TISSUE ABLATION EMPLOYING HIGH POWER DIODE-PUMPED LASER

(75) Inventors: Ming Lai, Rochester, NY (US); Liyue Mu, Fremont, CA (US); Kangze Cai, Fremont, CA (US); Weiguo Luo, Fremont, CA (US)

(73) Assignee: Applied Harmonics Corporation, Fremont, CA (US)

( * ) Notice: Subject to any disclaimer, the term of this patent is extended or adjusted under 35 U.S.C. 154(b) by 1371 days.

(21) Appl. No.: 11/155,079

(22) Filed: Jun. 17, 2005

(65) Prior Publication Data
US 2005/0288653 A1 Dec. 29, 2005

Related U.S. Application Data

(60) Provisional application No. 60/582,248, filed on Jun. 23, 2004.

(51) Int. Cl.
*A61B 18/18* (2006.01)
(52) U.S. Cl. ............... 606/10; 606/11; 606/13; 607/89
(58) Field of Classification Search ............ 606/1–15
See application file for complete search history.

(56) References Cited

U.S. PATENT DOCUMENTS

| | | | | |
|---|---|---|---|---|
| 4,675,872 A * | 6/1987 | Popek et al. | ............ | 372/10 |
| 5,066,291 A * | 11/1991 | Stewart | ............ | 606/3 |
| 5,151,909 A | 9/1992 | Davenport et al. | ............ | 372/22 |
| 5,312,396 A * | 5/1994 | Feld et al. | ............ | 606/11 |
| 5,694,408 A | 12/1997 | Bott et al. | ............ | 372/6 |
| 5,776,175 A | 7/1998 | Eckhouse et al. | ............ | 607/100 |
| 5,805,622 A | 9/1998 | Brinkmann | ............ | 372/9 |
| 6,009,110 A | 12/1999 | Wiechmann et al. | ............ | 372/10 |
| 6,031,854 A * | 2/2000 | Ming | ............ | 372/22 |
| 6,038,241 A | 3/2000 | Von Elm et al. | | |
| 6,156,030 A | 12/2000 | Neev | ............ | 606/10 |
| 6,309,352 B1 | 10/2001 | Oraevsky et al. | ............ | 600/407 |
| 6,413,267 B1 * | 7/2002 | Dumoulin-White et al. | ... | 607/89 |
| 6,482,199 B1 | 11/2002 | Neev | ............ | 606/10 |

(Continued)

OTHER PUBLICATIONS

Berger, "370mW, CW TEM00 Output From an Nd: YAG Laser Rod End-Pumped by a Monolithic Diod Array", Apr. 13, 1987.*

(Continued)

*Primary Examiner* — Sam Yao
*Assistant Examiner* — Lynsey Crandall
(74) *Attorney, Agent, or Firm* — Pillsbury Winthrop Shaw Pittman LLP

(57) ABSTRACT

The present invention discloses a high power diode-pumped laser for laser ablation of soft tissue. The present invention contemplates to operate the high power diode-pumped solid-state laser at a continuous Q-switching mode and at a big number of transverse modes. The present invention also contemplates to reduce beam divergence and beam spot size and thus to increase power density of the laser on target tissue to improve the speed of tissue ablation. The present invention further contemplates to minimize power consumption such that external water-cooling or secondary cooling loop can be eliminated. The present invention even further contemplates to implement combined mechanisms to protect intracavity optics from power damage. Finally, the present invention contemplates hospitals and surgeon offices to use the high power diode-pumped laser for soft tissue ablation with standard electrical wall-plug outlet and elimination of inconvenient external water-cooling or secondary cooling loop.

20 Claims, 2 Drawing Sheets

U.S. PATENT DOCUMENTS

| | | | |
|---|---|---|---|
| 6,554,824 B2* | 4/2003 | Davenport et al. | 606/3 |
| 6,723,090 B2 | 4/2004 | Altshuler et al. | 606/9 |
| 6,986,764 B2 | 1/2006 | Davenport et al. | 606/3 |
| 7,313,155 B1 | 12/2007 | Mu et al. | 372/10 |
| 7,769,059 B2 | 8/2010 | Mu et al. | 372/10 |
| 7,862,556 B2 | 1/2011 | Mu et al. | 606/10 |
| 2001/0031960 A1 | 10/2001 | Kliewer et al. | 606/5 |
| 2002/0003130 A1 | 1/2002 | Sun et al. | 219/121.68 |
| 2003/0058403 A1* | 3/2003 | Lai et al. | 351/212 |
| 2003/0130649 A1* | 7/2003 | Murray et al. | 606/3 |
| 2003/0135205 A1 | 7/2003 | Davenport et al. | |
| 2003/0156605 A1 | 8/2003 | Richardson et al. | 372/25 |
| 2004/0022280 A1* | 2/2004 | Lai et al. | 372/5 |
| 2004/0134894 A1 | 7/2004 | Gu et al. | 219/121.68 |
| 2004/0236319 A1 | 11/2004 | Davenport et al. | 606/3 |
| 2005/0027286 A1 | 2/2005 | Davenport et al. | 606/3 |
| 2005/0092720 A1 | 5/2005 | Gu et al. | 219/121.69 |
| 2005/0131400 A1 | 6/2005 | Hennings et al. | 606/15 |
| 2005/0256513 A1 | 11/2005 | Murray et al. | 606/3 |
| 2005/0288653 A1 | 12/2005 | Lai et al. | 606/10 |
| 2006/0007965 A1 | 1/2006 | Tankovich et al. | 372/10 |
| 2007/0225696 A1* | 9/2007 | Davenport et al. | 606/15 |

OTHER PUBLICATIONS

Malek et al., "High-Power Potassium-Titanyl-Phosphate (KTP/532) Laser Vaporization Porstatectomy: 24 Hours Later", Urology 51: 254-256, 1998, Elsevier Science Inc.

R.S. Kuntzman et al, "High-Power Potassium Titanyl Phosphate Laser Vaporization Prostatectomy", Mayo Clin Proc. 73:798-801, 1998.

R.S. Malek et al, "High Power Potassium-Titanyl-Phosphate Laser Vaporization Prostatectomy", J. of Urology, vol. 163, 1730-1733, 2000.

M. A. Hai et al, "Photoselective Vaporization of the Prostate: Initial Experience with a New 80W KTP Laser for the Treatment of BPH", J. of Endorology, vol. 17, (2), 2003.

Malek et al, "High-Power Potassium-Titanyl-Phosphate (KTP/532) Laser Vaporization Prostatectomy: 24 Hours Later", Urology, vol. 51, 1998, Elsevier Science Inc., pp. 254-256.

Randall S. Kuntzman et al., "High-Power Potassium Titanyl Phosphate Laser Vaporization Prostatectomy", Mayo Clinic Proc., vol. 73, 1998, pp. 798-801.

R. S. Malek et al, "High Power Potassium-Titanyl-Phosphate Laser Vaporization Prostatectomy", The Journal of Urology, vol. 163, Jun. 2000, pp. 1730-1733.

Mahmood A. Hai et al, "Photoselective Vaporization of the Prostate: Initial Experience with a New 80 W KTP Laser for the Treatment of Benign Prostatic Hyperplasia", Journal of Endourology, vol. 17, No. 2, Mar. 2003, pp. 93-96.

Walter Koechner, "Solid-State Laser Engineering", 5th Edition, Springer-Verlag Berlin Heidelerg, New York, 1999, 12 pages.

Anthony E. Siegman, "Lasers", University Science Books, Mill Valley, California, 1986, 26 pages.

"Photoselective Vaporization of the Prostate", Supplement to Urology Times, vol. 30, Supplement 1, May 2002, 20 pages.

Randall S. Kuntzman et al., "High-Power (60-Watt) Potassium-Titanyl-Phosphate Laser Vaporization Prostatectomy in Living Canines and in Human and Canine Cadavers", Urology, vol. 49, No. 5, 1997, Elsevier Science Inc., pp. 703-708.

Alfred Vogel et al, "Mechanisms of Pulsed Laser Ablation of biological Tissues", Chem. Rev., vol. 103, Published on Web Feb. 12, 2003, pp. 577-644.

Tuan Vo-Dinh, "Biomedical Photonics Handbook", CRC Press, 2003, pp. 2-1 to 2-75, 5-1 to 5-16.

V. V. Golovlyov et al., "Ablation of an Optically Homogeneous Absorbing Medium by Scattered Pulsed Laser Radiation", Applied Physics B, vol. 57, 1993, p. 451.

R. O. Esenaliev et al., "Laser Ablation of Aqueous Solutions with Spatially Homogeneous and Heterogeneous Absorption", Applied Physics B, vol. 59, 1994, p. 73.

Lawrence Livermore National Lab, "The Short-Pulse Laser: A Safe, Painless Surgical Tool", Science & Technology Review, Oct. 1995, 3 pages.

V. Venugopalan at al., "Thermodynamic Response of Soft Biological Tissues to Pulsed Infrared-Laser Irradiation", Biophysical Journal, vol. 70, Jun. 1996, pp. 2981-2993.

M. Ogura et al., "Myocardium Tissue Ablation with High-Peak-Power Nanosecond 1,064- and 532-nm Pulsed Lasers: Influence of Laser-Induced Plasma", Lasers in Surgery and Medicine, vol. 31, 2002, pp. 136-141.

J. Niamtu, "Clinical Applications of the 532-nm Diode Laser for the Treatment of Facial Telangiectasia and Pigmented Lesions: Literature Review, History, and Discussion of Clinical Experience", The American Journal of Cosmetic Surgery, vol. 18, No. 2, 2001, pp. 71-81.

S. Uhlhorn, "Free Electron Laser Ablation of Soft Tissue: The Effects of Chromophore and Pulse Characteristics of Ablation Mechanics", Ph.D. Dissertation, Vanderbilt University, Aug. 2002, 113 pages.

A. F. El-Sherif and T. A. King, "Soft and Hard Tissue Ablation with Short-Pulse High Peak Power and Continuous Thulium-Silica Fibre Lasers", Lasers Med. Sci, vol. 18, No. 3, 2003, p. 139.

A. Liu et al., "60-W Green Output by Frequency Doubling of a Polarized Yb-Doped Fiber Laser", Optics Letters, vol. 30, No. 1, Jan. 1, 2005, pp. 67-69.

F. H. Loesel et al., "Laser-Induced Optical Breakdown on Hard and Soft Tissues and Its Dependence on the Pulse Duration: Experiment and Model", IEEE Journal of Quantum Electronics, vol. 32, No. 10, Oct. 1996, pp. 1717-1722.

F. Sengor et al., "A Comparative Study of Laser Ablation and Transurethral Electroresection for Benign Prostatic Hyperplasia: Results of a 6-Month Follow-Up", British Journal of Urology, vol. 78, Issue 3, 1996, pp. 398.

M. Grasso et al., "Lasers in Urology", http://www.emedicine.com/med/topic3037.htm, Mar. 2006,15 pages.

Biswas, Dhruba J., et al., "Exploitation of Self-Focusing in the Operation of Optically Pumped Molecular Lasers", Applied Optics, vol. 29, No. 24, Aug. 20, 1990, pp. 3470-3472.

* cited by examiner

APPARATUS AND METHOD FOR SOFT TISSUE ABLATION EMPLOYING HIGH POWER DIODE-PUMPED LASER

This application claims the benefit of U.S. Provisional Application No. 60/582,248, filed on Jun. 23, 2004.

1. FIELD OF THE INVENTION

This invention relates in general to laser ablation of human soft tissue and in particular to high power laser ablation of prostate tissue.

2. BACKGROUND

Benign Prostatic Hyperplasia (BPH) can cause urinary frequency, dysuria and incomplete bladder emptying. The surgical "gold standard" for treating BPH has been the transurethral electrosurgical resection of obstructing prostatic tissue. Since its introduction some 50 years ago, transurethral resection of the prostate (TURP) has become the most widely used surgical therapy for BPH. Unfortunately, TURP associates with numerous side effects.

In the past decade, laser surgery has become an alternative to TURP for BPH treatment. High power laser beam is delivered to target prostatic tissue through an optical fiber that is introduced through an endoscope or cystoscope. Surgical outcome of laser treatment depends on a number of factors, including wavelength, power, and mode of operation (e.g., continuous or pulsed).

High power (60-80 W) Nd:YAG laser with a wavelength of 1064 nm was first used for BPH treatment in early 1990s. The advantage of Nd:YAG laser surgery is the laser's excellent hemostatic effect. At the wavelength of 1064 nm, laser light is absorbed by cellular proteins and penetrates approximately 7 mm into soft tissue. When soft tissue is heated to a certain temperature, it coagulates and shrinks. Nd:YAG laser treatment of obstructive BPH in general is not as effective as TURP.

High power (60-100 W) Ho:YAG laser with a wavelength of 2140 nm can be strongly absorbed by water and can thus evaporate soft tissue effectively. Ho:YAG laser surgery is a transurethral procedure and its clinical outcome is comparable with TURP. However, Ho:YAG laser surgery takes longer surgical time than TURP. Besides, it is technically challenging and has a steep learning curve.

High power (60-80 W) frequency-doubled Nd:YAG laser has been applied for BPH treatment since late 1990s. This laser has a wavelength at 532 nm and is transparent in water but selectively absorbed in soft tissue. This laser can effectively vaporize and ablate soft tissue and concurrently achieve hemostasis. The surgical outcome with this high power frequency-doubled Nd:YAG laser is comparable with TURP while the complication is significantly reduced.

Malek et al reported in 1998 that a 60 W frequency-doubled Nd:YAG (KTP/532) laser was used for laser vaporization prostatectomy and that the laser power was delivered continuously through an optical fiber onto prostatic tissue. Malek et al conclude in the report that "high-power KTP/532 laser vaporization prostatectomy is feasible and appears to be safe and effective for quickly relieving bladder outlet obstruction due to BPH". The report indicates a significant improvement in clinical outcome with 60 W KTP/532 laser over early 38 W KTP/532 laser. The report also indicates that the "KTP/532 laser energy was generated by a prototype Laserscope 800 series VHP (very high power) KTP/YAG laser generator delivering 60 W power continuously". The report further indicates that the laser has a spot diameter of 1.2 mm at 2 mm from the fiber tip, which translates into a big divergent angle, i.e., a numerical aperture of about 0.3. (See Malek et al., High-Power Potassium-Titanyl-Phosphate (KTP/532) Laser Vaporization Porstatectomy: 24 Hours Later, Urology 51: 254-256, 1998, Elsevier Science Inc.)

Davenport et al have later pointed out in U.S. Pat. No. 6,554,824 that "the problem with existing 532 nm lasers used to date is that they are large, expensive, inefficient and have a highly multi-mode output beam that makes them inefficient for ablating prostate tissue". In U.S. Pat. No. 6,554,824, Davenport et al disclose "operation of the solid-state laser in a 'macropulsed' mode is more efficient in inducing rapid tissue ablation than a CW laser of the same average power". Davenport et al also disclose that "the macropulsed laser is also more efficient and has higher beam quality, with $M^2$ values typically less than 144, than a continuous wave laser with same average output power". Davenport et al further disclose to generate a quasi-continuous wave (CW) beam having an output power exceeding 60 W or a high beam quality laser that "the number of transverse optical modes supported by the resonator needs to be kept as low as possible".

It is understood that operating a solid-state laser in a macropulsed mode can increase the macropulse peak power significantly and thus increase ablation efficiency. A limitation of operating a solid-state laser in a macropulsed mode is that requires higher and pulsed pump current, which leads to shorter component lifetime. Another limitation of operating a solid-state laser in a macropulsed mode is that produces a substantially higher peak power inside the laser cavity, which may lead to power damage of intracavity optics. When the diode laser is used to pump the solid-state laser, the drive macropulse can significantly reduce CW diode laser lifetime, even damage the diode laser, and shift the diode laser wavelength from its center wavelength.

It is also understood that reducing $M^2$ is helpful to obtain higher power densities that are required for rapid and efficient vaporization of prostate tissue. A limitation of operating a high power solid-state laser at low $M^2$ instead of high $M^2$ is that laser efficiency can be significantly lower and thus power consumption needs to be substantially higher. High power consumption of high power solid-state laser causes a series of inconvenience and additional expenses in hospital environment. High power consumption requires a high power outlet other than a standard wall-plug outlet. High power consumption requires external water-cooling or secondary cooling loop, which leads to extra system footage and operation cost. High power laser in general is very expensive electro-optical instrument. For the same output laser power, low efficiency laser has higher cost than a high efficiency laser. Another limitation of operating a high power solid-state laser at low $M^2$ instead of high $M^2$ is that power density at intracavity beam waist can be extremely high and power damage becomes a severe issue to fight.

It is further understood that operating a solid-state laser at higher average output power is helpful to obtain high power densities that are required for rapid and efficient vaporization of prostate tissue. A limitation of operating a solid-state laser at a power level substantially higher than 60 W requires substantially higher power consumption, which leads to a series of inconvenience and additional expenses in hospital environment. Another limitation of operating a solid-state laser at a power level substantially higher than 60 W is that power density at intracavity beam waist can be significantly higher, which may lead to power damage of intracavity optics.

It is even further understood that operating a high optical-to-electrical efficiency solid-state surgical laser at a power level substantially higher than 60 W can significantly reduce the system cooling capacity, eliminate the external water cooling requirement. Without requirements of external water cooling and input AC electrical current higher than 25 Amps, the high optical-to-electrical efficiency solid-state surgical laser can be easily installed in a standard surgery room. This advantage can encourage more hospitals and surgeon offices to use high power lasers in BPH treatment, such increase the consumption fiber-optic delivery devices.

3. SUMMARY OF THE INVENTION

The present invention recognizes the above limitations of high power frequency-doubled Nd:YAG (KTP/532) laser for laser vaporization prostatectomy and contemplates a high power diode-pumped solid-state laser to overcome the identified limitations. The present invention contemplates to operate the high power diode-pumped solid-state laser at a continuous Q-switching mode and at a big number of transverse modes. The present invention also contemplates to reduce beam divergence and beam spot size and thus to increase power density of the laser on target tissue to improve the speed of tissue ablation. The present invention further contemplates to minimize power consumption such that external water-cooling or secondary cooling loop can be eliminated. The present invention even further contemplates to implement combined mechanisms to protect intracavity optics from power damage.

In an embodiment, a prototype of surgical system for soft tissue treatment is constructed by employing a diode-pumped Nd:YAG laser. The diode-pumped laser is operated at a continuous Q-switching mode. The laser is frequency-doubled with an LBO crystal to produce laser output at 532 nm. The laser is configured to operate at a highly multiple modes to deliver a laser output of about 60 W. Power consumption of the laser is below 2 kW. First-pulse compression and temperature tuning are incorporated to prevent laser crystal and frequency-doubling crystal from laser power damage. Output laser beam is delivered through an optical fiber having a core diameter of 600 microns and a numerical aperture of 0.22. Coupling optics is implemented to minimize beam divergence angle and spot size at target tissue. Rapid laser ablation is observed on test tissues emerging in water.

Operating a diode-pumped laser at a continuous Q-switching mode allows continuous operation of the high power diode lasers that provide diode laser radiation to pump the solid-state laser. High power diode lasers have typically much longer lifetime in CW mode operation than in pulsed mode operation. Diode-pumped laser is also, for the same average output, less expensive to operate at CW mode than at pulsed mode.

Operating a solid-state laser at highly multiple modes creates a bigger beam size in laser crystal and in frequency-doubling crystal. Big beam size in laser crystal makes it less technical challenging and much more cost effective to achieve high power laser output. Big beam size in frequency-doubling crystal reduces power density and thus minimizes power damage at the crystal.

Operating a high power laser at highly multiple modes improves power conversion from electric power to laser power output. Power consumption can thus be made low enough such that the 60 W diode-pumped laser is operated with standard wall-plug outlet and there is no need for external water-cooling or secondary cooling loop. Lower power consumption also reduces operation cost of a surgical laser system. These advantages encourage more hospitals and surgeon offices to use such high power lasers in soft tissue laser ablation, such increase the consumption fiber-optic delivery devices.

Combining a first-pulse compressor and a temperature-tuning mechanism, along with operating at highly multiple modes, ensures multiple layers of protection of such a high power diode-pumped laser from laser power damage. A first-pulse compressor modifies the transient Q value of a Q-switched laser and eliminates the giant first-pulse that otherwise appears at each pulse train from a typical Q-switched laser. A temperature-tuning mechanism optimizes phase-matching angle of frequency-doubling crystal through temperature tuning and avoids temperature shock due to otherwise mechanical tuning of phase-matching angle.

Reducing beam divergence and beam spot size on target tissue increases laser power density and thus laser ablation rate. For application of laser vaporization prostatectomy, optical fiber is used to deliver laser power to target tissue. Coupling optics is elaborated to reduce beam divergence and to project laser power into a smaller spot than otherwise what a prior art laser system does. A reduced beam divergence leads to a slower power density change with distance between the fiber tip and target tissue, which will allow a surgeon to control laser ablation more easily in laser vaporization prostatectomy.

Accordingly, one objective of the present invention is to provide a new and improved high power diode-pumped laser for soft tissue ablation.

Another objective of the present invention is to provide a new and improved high power diode-pumped laser that uses a standard wall-plug outlet and requires no external water-cooling or secondary cooling loop.

A further objective of the present invention is to provide a new and improved high power diode-pumped laser that implements combined mechanisms to prevent intracavity optics from power damage.

Another further objective of the present invention is to provide a new and improved high power diode-pumped laser for laser vaporization prostatectomy.

The above and other objectives and advantages of the present invention will become more apparent in the following drawings, detailed description, and claims.

4. BRIEF DESCRIPTION OF THE FIGURES

5. DETAILED DESCRIPTION OF THE FIGURES

Figure 1:
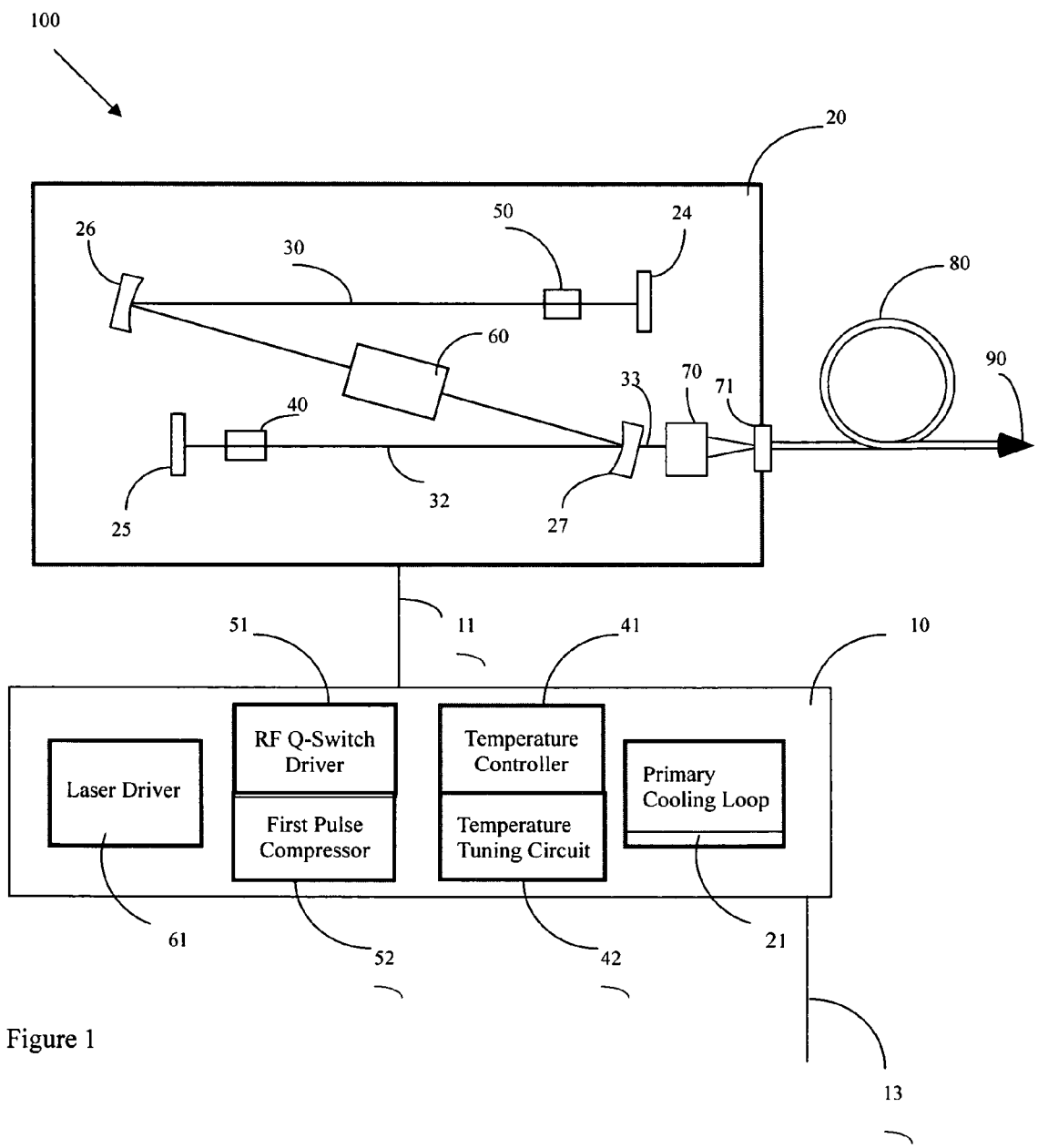
FIG. 1 is a schematic diagram showing an embodiment of a high power diode-pumped laser system for soft tissue ablation.

FIG. 1 is a schematic diagram showing an embodiment of a high power diode-pumped laser system 100 for soft tissue ablation. The laser system 100 is a diode-pumped Nd:YAG laser that is Q-switched and intracavity-frequency-doubled to produce a high power laser output 90 at a wavelength of 532 nm. The laser system 100 includes a laser head 20, a laser controller 10, and an optical fiber 80.

The laser head 20 consists of a pump head 60, a Q-switch 50, a second harmonic generator 40, and a folded resonant cavity formed by cavity mirror 24, cavity mirror 25, infrared folding mirror 26, and output coupler 27. The cavity mirror 24 and the infrared folding mirror 26 have high reflection coatings at 1064 nm. The cavity mirror 25 has a high reflection coating for both infrared and visible, e.g. at 1064 nm and 532 nm. The output coupler 27 has a high transmission at 532 nm and a high reflection at 1064 nm.

The pump head 60 consists of a solid-state gain medium of Nd:YAG laser rod. The laser rod is pumped with diode laser radiation delivered from multiple bars of high power diode lasers installed inside the pump head 60. The pump head 60 produces optical gain to generate fundamental laser radiation at 1064 nm. Other laser crystals such as Nd:YLF and Nd:YVO$_4$ may also be used for this application of soft tissue treatment.

The pump head 60 are preferably powered with CW current. Pump head for high power diode-pumped laser is a delicate and expensive component. High power diode lasers have typically much longer lifetime to operate at CW mode than at pulsed mode. The cost is also substantially lower to operate high power diode lasers at CW mode than at pulsed mode.

For a laser output of 40 to 140 W at 532 nm, the Nd:YAG laser rod inside the pump head 60 shall have a diameter of 2 mm or bigger, preferably 3 to 6 mm. The rod is side pumped with diode laser radiation form three or more directions. Side pump is a more economic geometry than end pump for high power laser output. Pumping a laser rod from three or more sides can substantially provide an angularly uniform gain distribution that leads to a better beam quality and higher conversion efficiency. Other crystal shape and pumping configuration such as slab or disk laser may also produce the desired laser power. For slab or disk laser, pump radiation from two directions is feasible.

The Q-switch 50 is an acoustic-optical modulator operating at a repetition rate of 5 to 40 kHz. When other gain medium is used, the Q-switch 50 shall be operable at a repetition rate within 1 to 100 kHz. The Q-switch 50 is used to increase the peak power of the diode-pumped laser and thus to improve the conversion efficiency of second harmonics generation. The Q-switch 50 is located near a cavity mirror 24 where the intracavity beam 30 is substantially collimated with a big beam size. A big and collimated beam allows a Q-switch to work more efficiently and more effectively, which results in shorter Q-switched pulse and more efficient harmonics generation and soft tissue ablation.

The second harmonics generator 40 converts the fundamental laser radiation at 1064 nm into second harmonic laser radiation at 532 nm. The second harmonic generator 40 consists of a frequency-doubling crystal such as LBO or KTP. LBO is more preferable for high power diode-pumped laser because it has as much as 5 times higher power damage threshold than KTP. The crystal is fabricated for either type I phase-matching or type II phase-matching. Each end surface of the crystal has an anti-reflection coating for both infrared (1064 nm) and visible (532 µm) wavelength. The second harmonic generator 40 is placed near cavity mirror 25 where the intracavity beam 32 is substantially collimated with a small beam size, i.e. a beam waist. A small and collimated beam allows second harmonics generation more efficiently.

As shown in FIG. 1, infrared laser beam path 30 is confined between cavity mirror 24 and cavity mirror 25, while visible laser beam path 32 is confined between cavity mirror 25 and output coupler 27. An output beam 33 with a wavelength at 532 nm exits from the output coupler 27. The output beam 33 is directed into a beam divergence controller 70 and then coupled into an optical fiber 80, of which a first end is mounted on a fiber mount 71. The beam divergence controller 70 and the fiber mount 71 form together a fiber coupler. A second end of fiber 80 delivers the laser output 90, in cooperating with an endoscope or cystoscope, to target tissue for treatment, including laser vaporization prostatectomy.

The laser controller 10 consists of a laser driver 61, a RF Q-switch driver 51, a first pulse compressor 52, a temperature controller 41, a temperature tuning circuit 42, and a primary cooling loop 21. The laser controller 10 is connected to laser head 20 via an umbilical cable 11 and is powered via power cable 13.

The laser driver 61 provides DC current to power diode lasers installed inside the pump head 60. The RF Q-switch driver 51 provides RF power to drive Q-switch 50. The temperature controller 41 maintains a stable temperature for the second harmonic generator 40. The primary cooling loop 21 provides direct water-cooling of the laser head 20. The primary cooling loop 21 removes heat generated inside the pump head 60, the RF Q-switch 50, and the second harmonic generator 40.

It is well known in the art that water-cooling of a high power laser is always a delicate and challenging task, requiring fast flow of distilled or deionized water. A primary cooling loop is typically a closed loop cooling system, enabling the use of distilled or deionized water. When power consumption is a few kilowatts or lower, heat carried by primary cooling loop may dissipate into the room through airflow. When power consumption is more than a few kilowatts, external water-cooling or a second cooling loop is a common solution to carry the heat out of the room where the high power laser is installed.

In this embodiment, laser cavity is designed to support a big number of transverse modes such that the mode volume matches well with the gain volume of a large laser rod of 5 mm in diameter and 118 mm in length. The input power to the pump head 60 is about 1.5 kilowatt when the diode-pumped laser operates at continuous Q-switching mode and produces a highly multiple-modes output of at least 80 W at 532 nm. Only a primary cooling loop 21 is used to cool the laser head 20. The total power consumption to the whole laser system 100 is less than 2 kW. A standard wall-plug outlet labeled 20A @ 110V is sufficient to power the laser system 100. (It is also common to see wall-plug outlet labeled 30A @ 110V, which can provide electric power up to 3 kW.)

The infrared folding mirror 26 and the output coupler 27 are spherical mirror to accommodate and control the cavity mode, in cooperating with thermal lens induced inside the laser rod located in the pump head 60. By design, the number of modes can be determined by the size of the laser rod and by the focal lengths of the infrared folding mirror 26 and the output coupler 27. The number of modes is typically much bigger than 10 for optimal power. Number of modes can possibly be so big that $M^2$ of the output beam 33 is great than 100. Number of modes can be reduced with shorter focal lengths of mirror 26 and output coupler 27 or with smaller diameter of laser rod, i.e. the laser rod services as a beam-size limiting element. In this sense, focal optics such as the infrared folding mirror 26 and output coupler 27 and beam-size limiting element such as the laser rod serve as mode control mechanisms to accommodate and control the number of modes to operate.

After the resonant cavity is constructed, output power can be optimized through varying repetition rate of the Q-switch 50 and crystal length of the second harmonics generator 40. Varying the repetition rate changes the peak power of intracavity pulse and thus changes conversion efficiency of harmonic generation. Varying the crystal length also results in a change in conversion efficiency of harmonic generation. In the above embodiment, the diode-pumped laser operated at highly multiple modes can have a conversion efficiency of about 6% from wall-plug electricity. Conversion efficiency may reduce to below 1% when operation mode is limited toward single transverse mode, i.e. TEM00 mode. Thus, multiple mode operation shall easily lead to a conversion efficiency of 3% or higher from wall-plug electricity.

Another delicate and challenging work with high power solid-state laser is to protect the laser crystal and frequency-doubling crystal from power damage. Operating the high power diode-pumped laser system 100 at highly multiple modes is a first measure to protect the crystals from power damage. Multiple-modes operation generates a much bigger beam size in either the laser crystal or the frequency doubling crystal and thus reduces the peak power density inside the crystals. Beam waist of this laser system 100 is about 5 to 50 times as big as what would be for a TEM00 mode.

A second measure implemented to protect the crystals is to compress the giant first-pulse of each Q-switched pulse train. When a Q-switch is suddenly switched on, initially stored energy turns into a giant first-pulse that may have a peak power significantly higher than other pulses. The first-pulse compressor 52 is used to incorporate with the Q-switch driver 51 and to modify the transient Q value of laser cavity to eliminate any giant first-pulses. One way to implement first-pulse compressor 52 is an electronic circuit to modify transient RF power applied to the Q-switch 50. Another way to implement a first-pulse compressor 52 is an electronic circuit to modify transient gate time of the Q-switch 50.

A third measure implemented to protect the frequency-doubling crystal is to tune crystal temperature slowly via a temperature tuning circuit 42. The second harmonic generator 40 is temperature regulated by a temperature controller 41 to maintain stable phase matching angle. Phase matching angle is a variable of temperature and mechanical position. Mechanical or temperature drift may deviate the phase matching condition from perfect. The temperature tuning circuit 42 is to tune and to compensate phase mismatching due to environment temperature and/or mechanical drift to optimal phase matching angle. Mechanical tuning would cause a temperature shock inside the frequency-doubling crystal due to a sudden change in optical path or heat loading. Such a temperature shock would damage the crystal easily. The temperature-tuning mechanism may eliminate to open laser cover during optimizing or servicing, thus further reducing possible human mistakes and improving laser reliability.

The laser system 100 as shown is designed for about 60 W to 140 W output power at 532 nm. Much higher output power can be obtained with two or more pump heads. Higher output power can also be obtained with two or more laser heads. Laser power of about 30 W to 100 W is preferable for effective ablation of soft tissue.

Effective laser ablation requires high power density on target tissue. Increasing the average power or operating the laser in a macro-pulsed mode is one approach to reach higher power density on target tissue. Confining laser power into a smaller spot on target tissue is another approach to improve laser ablation. For application where laser power is delivered to target tissue via an optical fiber, reducing beam divergence at the fiber tip is desirable to the second approach.

The beam divergence controller 70 is to change the beam size and to focus the output beam 33 into optical fiber 80 with a minimal loss and a feasibly small divergent angle. In one embodiment, the beam divergence controller 70 consists of a beam expander and a focal lens with a focal length of 25 mm. For a laser output beam 33 of highly multiple modes, the beam divergence measured after the optical fiber has still a numerical number smaller than 0.1, about ⅓ of the divergence reported by Malek et al. (See Malek et al., High-Power Potassium-Titanyl-Phosphate (KTP/532) Laser Vaporization Porstatectomy: 24 Hours Later, Urology 51: 254-256, 1998, Elsevier Science Inc. The report indicates that the laser has a spot diameter of 1.2 mm at 2 mm from the fiber tip, which translates into a big divergent angle, i.e., a numerical aperture of about 0.3.)

It shall be noted that the big numerical angle of 0.3 reported by Malek et al is not a necessary result of poor beam quality. For a very poor beam delivered from a 60 W KTP laser, as discussed in U.S. Pat. No. 6,554,824 to Davenport et al, the beam quality has a $M^2$ value of 144. In this circumstance, the beam divergent angle shall be about 12 times as big as a Gaussian beam. Calculation shows that the divergent angle of such a poor beam with $M^2=144$ shall have a low limit to its numerical aperture of about 0.1. The divergent angle as reported by Malek et al is thus far from minimized. A feasibly small beam divergence angle shall have a numerical aperture of 0.2 or smaller.

The numerical aperture of the optical fiber 80 defines an up-limit of divergence angle for the beam delivered through the fiber. Large core fiber (e.g. 600 micro in diameter) used for laser vaporization prostatectomy may have a numerical aperture of 0.22 or higher. To achieve efficient laser ablation with a 60 W laser, it is greatly desirable to have a beam divergence with a numerical aperture of 0.15 or smaller. The beam divergence controller 70 shall minimize the coupling loss of the output beam 33 into the optical fiber 80 and meanwhile minimize the divergence angle of the coupled beam.

For a diode-pumped laser 100 operated at highly multiple modes, a fiber core with a diameter of 400 to 1000 micro shall be used. The numerical aperture of the optical fiber 80 shall be 0.12 or bigger, preferably 0.22. The beam divergence controller 70 can be simply a focal lens with a focal length 35 to 50 times of the spot size of the output beam 33 upon the lens. For a TEM00 mode operation, such a beam divergence controller 70 produces a diffraction limited beam divergence of about 0.015 to 0.01 and a beam spot of about 20 to 30 micro on the fiber inlet surface. For a highly multiple modes operation with a beam divergence ten times of diffraction limit, for instance, the beam divergence is about 0.15 to 0.1 and the beam spot is about 200 to 300 micro on the fiber inlet surface. Low-loss coupling is achieved to a 600 micro fiber with a numerical aperture of 0.22. For a diode-pumped laser 100 operated at highly multiple modes, the beam divergence measured after the optical fiber 80 has a numerical aperture smaller than 0.1.

In addition to the beam divergent controller 70, beam divergence and beam spot can be further reduced with focal optics positioned at the output end of the optical fiber 80. FIGS. 2 through 5 show prior art and modified fiber tips to implement focal optics.

Figure 2:
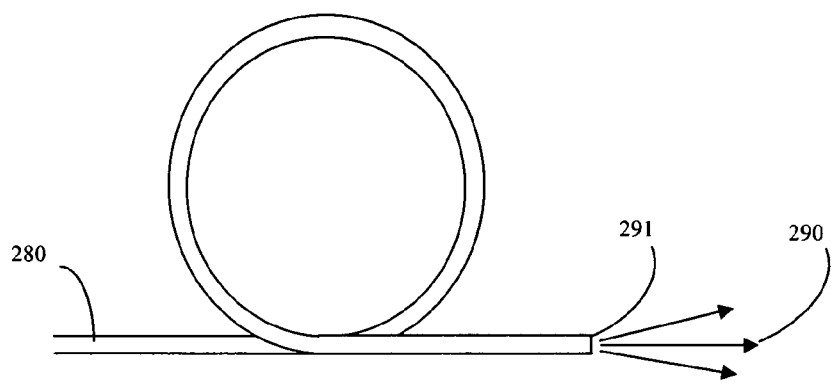
FIG. 2 illustrates a prior art fiber tip.

FIG. 2 illustrates a prior art fiber tip 291 of optical fiber 280. The facet of the fiber tip 291 is a flat polished surface, and output beam 290 is a divergent beam. The divergent angle of the beam depends on the beam quality, as well as numerical aperture of the optical fiber 280. For a large core fiber, such as the 600-micro fiber used in prior art laser vaporization prostatectomy, laser beam quality is attributed to an undesirably big divergent angle.

Figure 3:
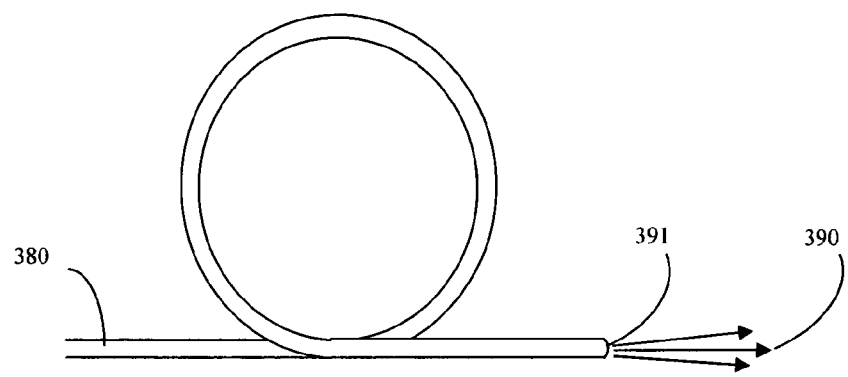
FIG. 3 illustrates a modified fiber tip.

FIG. 3 illustrates a modified fiber tip 391 of optical fiber 380. The facet of the fiber tip 391 is a curved surface, and output beam 390 is a less divergent beam. A less divergent output beam 390 shall have a smaller beam spot and thus a higher power density on target tissue, in comparing to an otherwise divergent beam 290. A less divergent output beam 390 shall also lead to a slower power density change with respect to distance between the fiber tip 391 and the target tissue, which allows a surgeon to control more easily laser ablation on target tissue.

Figure 4:
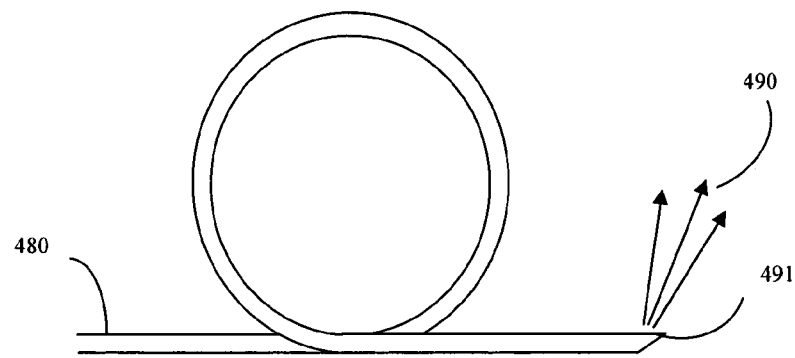
FIG. 4 illustrates another prior art fiber tip.

FIG. 4 illustrates another prior art fiber tip 491 of optical fiber 480. The facet of the fiber tip 491 is a flat but inclined surface, and output beam 490 is a divergent beam deflected to one side of the optical fiber 480.

Figure 5:
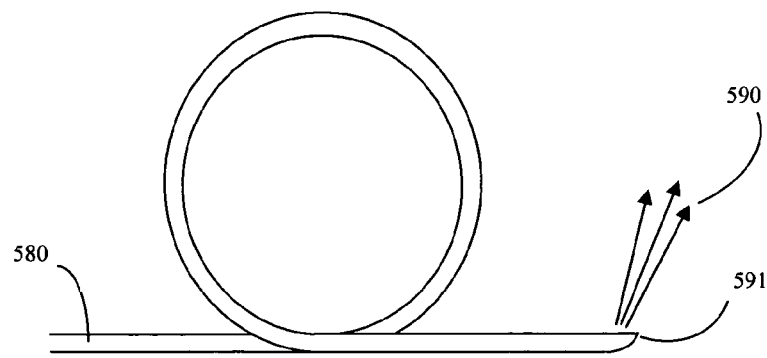
FIG. 5 illustrates another modified fiber tip.

FIG. 5 illustrates another modified fiber tip 591 of optical fiber 580. The facet of the fiber tip 591 is a curved and inclined surface, and output beam 590 is a less divergent beam deflected to one side of the optical fiber 580. A less divergent output beam 590 shall have a smaller beam spot and thus a higher power density on target tissue, in comparison with an otherwise divergent beam 490. A less divergent output beam 590 shall also lead to a slower power density change with respect to distance between the fiber tip 591 and target tissue aside from the tip, which shall allow a surgeon to control more easily laser ablation on target tissue aside form the fiber 580.

Although FIG. 3 and FIG. 5 illustrate a focal optics modified from a fiber tip, focal optics can have other form and configuration. Focal optics can be a micro-optics integrated onto the fiber tip or separated from the tip.

Although the above description is based on preferred embodiments to illustrate the present invention, various modifications can be made without departing from the scopes of the appended claims.

What is claimed is:

1. A surgical apparatus for laser ablation of soft tissue, comprising:
    a laser operated at highly multiple modes and producing an output laser beam of 40 W or higher, said laser including:
        a resonant optical cavity;
        a gain medium deposited in said resonant optical cavity;
        a plurality of pump radiation sources configured to pump said gain medium from two or more directions;
        a Q-switch deposited in said resonant cavity and being operable at a repetition rate within 1 kHz to 100 kHz;
        a frequency-doubling crystal deposited in said resonant cavity to receive radiation emitted by said gain medium; and
        a mode control mechanism implemented in said resonant cavity and ensuring highly multiple modes to operate, wherein a beam spot size at said gain medium is at least five times as big as a minimum beam spot size associated with TEM00 mode operation;
    an optical fiber configured to output radiation from the apparatus onto soft tissue to ablate the soft tissue; and
    a beam divergence controller configured to receive radiation output from said resonant optical cavity, and to output the received radiation to the optical fiber, wherein the beam divergence controller processes the radiation received from said resonant optical cavity prior to outputting the received radiation to the optical fiber such that the beam divergence angle of the radiation output from the optical fiber to said soft tissue is reduced.

2. A surgical apparatus for laser ablation of soft tissue, comprising:
    a laser operated in continuous wave mode at highly multiple transverse modes and producing an output laser beam of 40 W or higher, said laser including:
        a resonant optical cavity;
        a gain medium deposited in said resonant optical cavity;
        a plurality of pump radiation sources configured to pump gain medium from two or more directions according to a continuous wave mode;
        a Q-switch deposited in said resonant optical cavity and being operable at a repetition rate within 1 kHz to 100 kHz;
        a frequency-doubling crystal deposited in said resonant optical cavity to receive radiation emitted by said gain medium; and
        a mode control mechanism implemented in said resonant cavity and ensuring highly multiple modes to operate, wherein a beam spot size at said gain medium is at least five times as big as a minimum beam spot size associated with TEM00 mode operation; and
    a beam delivery optics configured to deliver radiation output from the resonant optical cavity to soft tissue for ablation, wherein the beam delivery optics include one or more optical members that reduce the beam divergence angle of the radiation output from an optical fiber to the soft tissue.

3. A surgical apparatus of claim 1, further comprising a first-pulse compressor coupled electronically to said laser and configured to eliminate giant first-pulses from any train of said Q-switched pulses of radiation emitted by the laser.

4. A surgical apparatus of claim 1 wherein said soft tissue includes prostatic tissue.

5. A surgical apparatus of claim 1 wherein said laser operates at a continuous mode Q-switching mode.

6. A surgical apparatus of claim 1 wherein said highly multiple modes has 10 or more modes.

7. A surgical apparatus of claim 1 wherein said laser delivers 30 W to 150 W laser power on said soft tissue.

8. A surgical apparatus of claim 1 wherein said gain medium includes Nd:YAG, Nd:YLF, or Nd:YVO$_4$.

9. A surgical apparatus of claim 1 wherein pump radiation from the pump radiation sources is generated with continuous wave current.

10. A surgical apparatus of claim 1 wherein said frequency-doubling crystal includes LBO or KTP.

11. A surgical apparatus of claim 1 wherein said output laser beam has a beam quality with value $M^2$ greater than 100.

12. A surgical apparatus of claim 1 wherein said mode control mechanism comprises focal optics with predetermined focal length to ensure operation of said highly multiple modes.

13. A surgical apparatus of claim 1 wherein said laser delivers laser output from one or more laser heads.

14. A surgical apparatus of claim 1 wherein said beam divergence angle has a numerical aperture of 0.2 or smaller.

15. A surgical apparatus of claim 1, further comprising a beam-size control element implemented with said beam delivery optics and configured to control beam size of said output laser beam on said soft tissue to obtain an improved ablation speed.

16. A surgical apparatus of claim 2 further comprising a Q-switch controller that enhances power efficiency of said laser via repetition rate and peak power of Q-switched pulses.

17. A surgical apparatus of claim 2 wherein said frequency-doubling crystal that enhances power efficiency of said laser via crystal length.

18. A surgical apparatus of claim 2 wherein said power consumption of said laser is 3 kilowatt or lower.

19. A surgical apparatus of claim 2 wherein said power consumption of said laser is sufficiently low to enable usage in a clinical setting without external water-cooling or a secondary cooling loop.

20. A surgical apparatus of claim 2 wherein the beam delivery optics comprise an optical fiber with a surface that has been formed to reduce the beam divergence angle of the radiation delivered by the optical fiber to the soft tissue.

* * * * *